(12) United States Patent
Mangin et al.

(10) Patent No.: US 11,773,163 B2
(45) Date of Patent: Oct. 3, 2023

(54) METHODS AND PHARMACEUTICAL COMPOSITIONS FOR THE PROPHYLACTIC TREATMENT OF METASTASES

(71) Applicants: INSERM (INSTITUT NATIONAL DE LA SANTÉ ET DE LA RECHERCHE MÉDICALE), Paris (FR); UNIVERSITÉ DE STRASBOURG, Strasbourg (FR); ETABLISSEMENT FRANçAIS DU SANG (EFS), La Plaine Saint Denis (FR)

(72) Inventors: Pierre Mangin, Strasbourg (FR); Christian Gachet, Strasbourg (FR)

(73) Assignees: INSERM (INSTITUT NATIONAL DE LA SANTÉ ET DE LA RECHERCHE MÉDICALE), Paris (FR); UNIVERSITÉ DE STRASBOURG, Strasbourg (FR); ETABLISSEMENT FRANçAIS DU SANG (EFS), La Plaine Saint Denis (FR)

( * ) Notice: Subject to any disclaimer, the term of this patent is extended or adjusted under 35 U.S.C. 154(b) by 344 days.

(21) Appl. No.: 16/462,754

(22) PCT Filed: Nov. 21, 2017

(86) PCT No.: PCT/EP2017/079847
§ 371 (c)(1),
(2) Date: May 21, 2019

(87) PCT Pub. No.: WO2018/091720
PCT Pub. Date: May 24, 2018

(65) Prior Publication Data
US 2019/0315862 A1    Oct. 17, 2019

(30) Foreign Application Priority Data
Nov. 21, 2016    (EP) .................................... 16306520

(51) Int. Cl.
| | | |
|---|---|---|
| *A61K 39/395* | (2006.01) |
| *C07K 16/28* | (2006.01) |
| *A61P 35/04* | (2006.01) |
| *C07K 14/705* | (2006.01) |
| *C12N 15/115* | (2010.01) |
| *A61K 39/00* | (2006.01) |

(52) U.S. Cl.
CPC .......... *C07K 16/2803* (2013.01); *A61P 35/04* (2018.01); *C07K 14/70503* (2013.01); *C12N 15/115* (2013.01); *A61K 2039/505* (2013.01); *C07K 2317/55* (2013.01); *C07K 2317/565* (2013.01); *C07K 2319/30* (2013.01); *C12N 2310/16* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 9,045,538 B2 * | 6/2015 | Jandrot-Perrus | .......... A61P 9/00 |
| 2004/0001826 A1 * | 1/2004 | Gill | .................... C07K 16/2803 |
| | | | 424/143.1 |
| 2009/0130021 A1 | 5/2009 | Munch | |
| 2011/0044993 A1 * | 2/2011 | Kronthaler | .............. A61P 35/04 |
| | | | 424/143.1 |

FOREIGN PATENT DOCUMENTS

EP          1 916 259 A1    4/2008

OTHER PUBLICATIONS

Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368. doi: 10.1038/S41577-019-0126-7.*
Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Zhuyan et al., Cell Biosci. Jul. 28, 2020;10:89. doi: 10.1186/s13578-020-00453-9. eCollection 2020.*
M. Al-Tamimi et al: "Focusing on plasma glycoprotein VI", Thrombosis and Haemostasis, vol. 107, No. 4, Jan. 25, 2012, pp. 648-655.
J. N. Hahn et al: "The role of EMMPRIN in T cell biology and immunological diseases", Journal of Leukocyte Biology, vol. 98, No. 1, May 14, 2015, pp. 33-48.

* cited by examiner

*Primary Examiner* — Michael Szperka
(74) *Attorney, Agent, or Firm* — WCF IP (57) ABSTRACT

The present invention relates to methods and pharmaceutical compositions for the prophylactic treatment of metastases. The inventors showed in vivo that lung metastasis in GPVI deficient mice are reduced compared to controls. They demonstrated that GPVI is involved in platetet interaction with tumor cells and this interaction is mediated by EMMPRIN.). Using an anti-EMMPRIN antibody, they showed that the adhesion of platelets to tumors cells is decreased. In particular, the present invention relates to a method for the prophylactic treatment of metastases in a patient suffering from cancer comprising administering to the subject a therapeutically effective amount of an agent which inhibits the interaction between GPVI and EMMPRIN.

4 Claims, 5 Drawing Sheets
Specification includes a Sequence Listing.

SEQUENCE LISTING

<160> NUMBER OF SEQ ID NOS: 6

<210> SEQ ID NO 1
<211> LENGTH: 10
<212> TYPE: PRT

-continued

```
<213> ORGANISM: Artificial
<220> FEATURE:
<223> OTHER INFORMATION: Synthetic VH CDR1

<400> SEQUENCE: 1

Gly Tyr Thr Phe Thr Ser Tyr Asn Met His
1               5                   10

<210> SEQ ID NO 2
<211> LENGTH: 17
<212> TYPE: PRT
<213> ORGANISM: Artificial
<220> FEATURE:
<223> OTHER INFORMATION: Synthetic VH CDR2

<400> SEQUENCE: 2

Gly Ile Tyr Pro Gly Asn Gly Asp Thr Ser Phe Asn Gln Lys Phe Lys
1               5                   10                  15

Gly

<210> SEQ ID NO 3
<211> LENGTH: 11
<212> TYPE: PRT
<213> ORGANISM: Artificial
<220> FEATURE:
<223> OTHER INFORMATION: Synthetic VH CDR3

<400> SEQUENCE: 3

Gly Thr Val Val Gly Asp Trp Tyr Phe Asp Val
1               5                   10

<210> SEQ ID NO 4
<211> LENGTH: 16
<212> TYPE: PRT
<213> ORGANISM: Artificial
<220> FEATURE:
<223> OTHER INFORMATION: Synthetic VL CDR1

<400> SEQUENCE: 4

Arg Ser Ser Gln Ser Leu Glu Asn Ser Asn Gly Asn Thr Tyr Leu Asn
1               5                   10                  15

<210> SEQ ID NO 5
<211> LENGTH: 7
<212> TYPE: PRT
<213> ORGANISM: Artificial
<220> FEATURE:
<223> OTHER INFORMATION: Synthetic VL CDR2

<400> SEQUENCE: 5

Arg Val Ser Asn Arg Phe Ser
1               5

<210> SEQ ID NO 6
<211> LENGTH: 9
<212> TYPE: PRT
<213> ORGANISM: Artificial
<220> FEATURE:
<223> OTHER INFORMATION: Synthetic VL CDR3

<400> SEQUENCE: 6

Leu Gln Leu Thr His Val Pro Trp Thr
1               5
```

METHODS AND PHARMACEUTICAL COMPOSITIONS FOR THE PROPHYLACTIC TREATMENT OF METASTASES

FIELD OF THE INVENTION

The present invention relates to methods and pharmaceutical compositions for the prophylactic treatment of metastases.

BACKGROUND OF THE INVENTION

Cancer, and in particular breast cancer, remains a major public health concern. The formation of distant metastases remains a challenge, as this constitutes the main cause of death in this pathology. Metastasis occurs in sequential steps: i) detachment of tumor cells from the primary tumor and intravasation into the blood or lymphatic circulation; ii) journey in the bloodstream during which tumor cells physically and functionally interact with blood cells; iii) adhesion to the endothelium at distant sites; iv) extravasation and colonization of distant sites and finally v) growth of metastases.

Platelets play a central role in the arrest of bleeding. A set of arguments indicates that platelets are involved in tumor dissemination, notably an increased circulating platelet count is associated with a poor cancer prognosis. Platelets are proposed to support metastasis through interaction with circulating tumor cells (CTCs). Platelets activated by tumor cells could: i) protect them from the immune system; ii) induce epithelial to mesenchymal transition; iii) facilitate their arrest at the vessel wall, and iv) promote their extravasation at distant sites. Moreover, platelets are able to guide the establishment of metastatic niches within first hours of metastasis, and could modulate metastasis through interaction with neutrophils. While many roles for platelets were proposed, the mechanisms involved in platelet-tumor cell interactions remain poorly understood and their identification will provide a basis to interfere with platelet-dependent tumor cell dissemination and thereby open new therapeutic anti-cancer avenues.

GPVI is a platelet specific receptor for collagen, considered as a safe anti-thrombotic target. Jain and collaborators described a role for GPVT in experimental metastasis (Jain, S et al. 2009. "Platelet Glycoprotein VI Facilitates Experimental Lung Metastasis in Syngenic Mouse Models." Journal of Thrombosis and Haemostasis 7(10): 1713-17.). The authors reported that administration of B16F10 or LLC tumor cells in the tail vein of GPVI-deficient mice resulted in a marked reduction in tumor cell colonization to the lungs. WO2009/129980 teaches that depletion of platelet with anti-GPVI antibody could be suitable for the prevention and treatment of cancer. However, the mechanism by which GPVI promotes metastasis remains completely unknown.

SUMMARY OF THE INVENTION

The present invention relates to methods and pharmaceutical compositions for the prophylactic treatment of metastases. In particular, the present invention is defined by the claims.

DETAILED DESCRIPTION OF THE INVENTION

The first object of the present invention relates to a method for the prophylactic treatment of metastases in a patient suffering from cancer comprising administering to the subject a therapeutically effective amount of an agent which inhibits the interaction between GPVI and EMMPRIN.

As used herein the term "metastasis" has its general meaning in the art and refers to the transmission of cancerous cells from the primary tumor to one or more sites elsewhere in a patient causing secondary, metastatic tumors. A tumor formed by cells that have spread is called a "metastatic cancer" or "metastasis", e.g. a lung metastasis. The metastasis contains cells originating from the primary tumor or the secondary, metastatic tumor, but differs from the primary or secondary, metastatic tumor e.g. by the site of primary or secondary, metastatic tumor. For instance, the site of primary or secondary, metastatic tumor is a breast cancer and the metastasis is a lung metastasis. Means to determine if a cancer has metastasized are known in the art and include tumor marker tests, bone scan, chest X-ray, computed tomography (CT), computerized axial tomography (CAT), molecular resonance imaging (MRI), positron emission tomography (PET), single photon emission computed tomography (SPECT), fluorescence imaging (FI), and bioluminescent imaging (BLI) (see e.g. Helms, M. W, et al, Contributions to microbiology 13 (2006) 209-231 and Pantel, K., et al., JNCI 91 (1999) 1113-1124).

In some embodiments, the method of the present invention is particularly suitable for the prophylactic treatment of lung metastases.

The term "lung metastasis," as used herein, refers to the transfer of malignant cells to one or more sites within lung not directly connected with the first site, after which the cells form a proliferative focus within the lung. The resulting detached masses of cancer cells within the lung are termed lung "metastases" or secondary tumors. Lung metastases can originate from a variety of primary cancers, which they generally will resemble histologically. Breast cancer, kidney cancer and melanoma, for example, frequently metastasize to lung. In addition, cancers of the bladder, cervix, ovary and prostate metastasize to lung and, less frequently, colorectal cancers or primary lung cancers metastasize to one or more secondary sites in lung.

As uses herein the term "prophylactic treatment" has its general meaning in the art and and refers to any medical or public health procedure whose purpose is to prevent a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a subject with the disease. It is also to be appreciated that the various modes of treatment or prevention of medical conditions as described are intended to mean "substantial," which includes total but also less than total treatment or prevention, and wherein some biologically or medically relevant result is achieved.

In some embodiments, the patient suffers from a cancer selected from the group consisting of bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating, lobular carcinoma, lobular carcinoma in, situ, gynecomastia), Castleman disease (e.g. giant lymph node hyperplasia, angio follicular lymph node hyperplasia), cervical cancer, colorectal cancer, endometrial cancer (e.g. endometrial adenocarcinoma, adenocanthoma, papillary serous adnocarcinroma, clear cell), esophagus cancer, gallbladder cancer (mucinous adenocarcinoma, small cell carcinoma), gastrointestinal carcinoid tumors (e.g. choriocarcinoma, chorioadenoma *destruens*), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

In some embodiments, the patient suffers from an advanced cancer. As used herein, the term "advanced cancer" refers to a stage of cancer in which the disease has spread by metastasis from the primary site (primary tumor) to other parts of the body, directly or by traveling through the network of lymph glands (lymphatics) or in the bloodstream and thus forming metastasis. When the cancer has spread only to the surrounding areas e.g. to nearby tissues or lymph nodes, it is called locally advanced.

In some embodiments, the patient suffers from a breast cancer. As used herein, the term "breast cancer" refers to the uncontrolled growth of abnormal breast cells. It includes ductal carcinoma in situ, invasive ductal carcinoma, lobular carcinoma in situ, invasive lobular carcinoma, medullary carcinoma, Paget's disease of the nipple and metastatic breast cancer. In some embodiments, the patient suffers from triple negative breast cancer. As used herein, the term "triple negative breast cancer" has its general meaning in the art and means that said breast cancer lacks receptors for the hormones estrogen (ER– negative) and progesterone (PR-negative), and for the protein HER2.

As used herein, the term "GPVI" has its general meaning in the art and refers to a platelet membrane glycoprotein of the immunoglobulin superfamily encoded by the GP6 gene (Gene ID: 51206). The term GPVI is also known BDPLT11. Exemplary human nucleic acid and amino acid sequences are represented by the NCBI references sequences respectively NM_001083899.2 and NP_001077368.2.

As used herein, the term "EMMPRIN" has its general meaning in the art and refers to a the Extracellular Matrix Metalloproteinase Inducer encoded by the BSG gene (Gene ID: 682). The term is also known as basigin, 5F7; TCSF; or CD147. Exemplary human nucleic acid and amino acid sequences are represented by the NCBI references sequences respectively NM_001728. and NP_001719.2.

As used herein the expression "agent that inhibits the interaction between GPVI and EMMPRIN" refers to any compound that is capable of inhibiting the interaction between GPVI and EMMPRIN, in particular the binding of GPVI to EMMPRIN.

In some embodiments, the agent is an antibody. In some embodiments, the antibody is an antibody having specificity for GPVI. In some embodiments, the antibody is an antibody having specificity for EMMPRIN.

As used herein, the term "antibody" has its general meaning in the art and encompasses monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

In some embodiments, the antibody of the present invention is a monoclonal antibody. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, monoclonal antibodies are advantageous in that they can be synthesized by hybridoma cells that are uncontaminated by other immunoglobulin producing cells. Alternative production methods are known to those trained in the art, for example, a monoclonal antibody may be produced by cells stably or transiently transfected with the heavy and light chain genes encoding the monoclonal antibody. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with the appropriate antigenic forms (i.e. polypeptides of the present invention). The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes. Briefly, the recombinant polypeptide of the present invention may be provided by expression with recombinant cell lines. Recombinant forms of the polypeptides may be provided using any previously described method. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods. Following culture of the hybridomas, cell supernatants are analysed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

In some embodiments, the monoclonal antibody of the invention is a chimeric antibody, in particular a chimeric mouse/human antibody. As used herein, the term "chimeric antibody" refers to an antibody which comprises a VH domain and a VL domain of a non-human antibody, and a CH domain and a CL domain of a human antibody. In some embodiments, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

In some embodiments, the monoclonal antibody of the invention is a humanized antibody. In particular, in said humanized antibody, the variable domain comprises human acceptor frameworks regions, and optionally human constant domain where present, and non-human donor CDRs, such as mouse CDRs. According to the invention, the term "humanized antibody" refers to an antibody having variable region framework and constant regions from a human antibody but retains the CDRs of a previous non-human antibody. The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like. Methods for producing humanized antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

In some embodiments the antibody of the invention is a human antibody. As used herein the term "human antibody is intended to include antibodies having variable and constant regions derived from human immunoglobulin sequences. The human antibodies of the present invention may include amino acid residues not encoded by human immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. Human antibodies can be produced using various techniques known in the art. Human antibodies are described generally in van Dijk and van de Winkel, cur. Opin. Pharmacol. 5; 368-74 (2001) and lonberg, cur. Opin. Immunol. 20; 450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23; 1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application publication No. US 2007/0061900, describing VELOCIMOUSE® technology. Human variable regions from intact antibodies generated by such animals may be further modified, e.g., by combining with a different human constant region Human antibodies can also be made by hybridoma-based methods. Human myeloma and mouse-human heteromyeloma cell lines for the production of human monoclonal antibodies have been described. (See, e.g., Kozbor J. Immunol., 13: 3001 (1984); Brodeur et al., Monoclonal Antibody Production Techniques and Applications, pp. 51-63 (Marcel Dekker, Inc., New York, 1987); and Boerner et al., J. Immunol., 147: 86(1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human igM antibodies from hybridoma cell lines) and Ni, Xiandai Mianyixue, 26(4): 265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005). Fully human antibodies can also be derived from phage-display libraries (as disclosed in Hoogenboom et al., 1991, J. Mol. Biol. 227: 381; and Marks et al., 1991, J. Mol. Biol. 222:581). Phage display techniques mimic immune selection through the display of antibody repertoires on the surface of filamentous bacteriophage, and subsequent selection of phage by their binding to an antigen of choice. One such technique is described in PCT publication No. WO 99/10494. Human antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In some embodiments, the antibody of the present invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®".

In some embodiments, the anti GPVI antibody of the present invention does not induce depletion of platelets. As used herein, the term "depleting", with respect to platelets, means a process, method, or compound that can kill, eliminate, lyse or induce such killing, elimination or lysis, so as to negatively affect the number of platelets in the patient. In some embodiments, the anti-GPVI antibody of the present invention does not mediate antibody-dependent cell-mediated cytotoxicity and thus does not comprise an Fc portion that induces antibody dependent cellular cytotoxicity (ADCC). In some embodiments the anti-GPVI antibody of the present invention does not lead, directly or indirectly, to the depletion of cells expressing GPVI such as platelets (e.g. do not lead to a 10%, 20%, 50%, 60% or greater elimination or decrease in number of cells expressing GPVI). In some embodiments, the antibody of the present invention lacks an Fc domain (e.g. lacks a CH2 and/or CH3 domain) or comprises an Fc domain of IgG2 or IgG4 isotype. As used herein the term "antibody-dependent cell-mediated cytotoxicity" or 'ADCC" refer to a cell-mediated reaction in which non-specific cytotoxic cells (e.g., Natural Killer (NK) cells, neutrophils, and macrophages) recognize bound antibody on a target cell and subsequently cause lysis of the target cell. While not wishing to be limited to any particular mechanism of action, these cytotoxic cells that mediate ADCC generally express Fc receptors (FcRs).

In some embodiments, the anti-GPVI antibody of the present invention is a Fab. As used herein, the term "Fab" refers to an antibody fragment that consists of an entire L chain (VL and CL) along with the variable region domain of the H chain (VH), and the first constant domain of one heavy chain (CH1). Papain digestion of an intact antibody can be used to produce two Fab fragments, each of which contains a single antigen-binding site. Typically, the L chain and H chain fragment of the Fab produced by papain digestion are linked by an interchain disulfide bond.

In some embodiments, the anti-GPVI antibody of the present invention (e.g. the anti-GPVI Fab) comprises a heavy chain variable region comprising CDR1, CDR2 and CDR3 regions constituted of SEQ ID NO: 1, SEQ ID NO: 2, and SEQ ID NO: 3 and a light chain variable region comprising CDR1, CDR2 and CDR3 regions constituted of SEQ ID NO: 4, SEQ ID NO: 5, and SEQ ID NO: 6 (i.e. 9O12 antibody).

| | | (SEQ ID NO: 1) |
|---|---|---|
| VH CDR1 | GYTFTSYNMH | |
| VH CDR2 | GIYPGNGDTSFNQKFKG | (SEQ ID NO: 2) |
| VH CDR3 | GTVVGDWYFDV | (SEQ ID NO: 3) |
| VL CDR1 | RSSQSLENSNGNTYLN | (SEQ ID NO: 4) |
| VL CDR2 | RVSNRFS | (SEQ ID NO: 5) |
| VL CDR3 | LQLTHVPWT | (SEQ ID NO: 6) |

In one embodiment, the agent is an aptamer that inhibits the interaction between GPVI and EMMPRIN. In some embodiments, the agent is an apatamer having specificity for GVPI or EMMPRIN. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Peptide aptamers consists of a conformationally constrained antibody variable region displayed by a platform protein, such as E. coli Thioredoxin A that are selected from combinatorial libraries by two hybrid methods.

In some embodiments, the agent is a polypeptide. In some embodiments, the agent is a polypeptide which is a functional equivalent of GPVI or EMMPRIN. As used herein, a "functional equivalent" of GPVI is a compound which is capable of binding to EMMPRIN, thereby preventing its interaction with GPVI. As used herein, a "functional equivalent" of EMMPPRIN is a compound which is capable of binding to GPVI, thereby preventing its interaction with EMMPRIN. The term "functional equivalent" includes fragments, mutants, and muteins of GPVI or EMMPRIN. The term "functionally equivalent" thus includes any equivalent of GPVI obtained by altering the amino acid sequence, for example by one or more amino acid deletions, substitutions or additions such that the protein analogue retains the ability to bind to its ligand. Amino acid substitutions may be made, for example, by point mutation of the DNA encoding the amino acid sequence. Functional equivalents include molecules that comprise all or a portion of the extracellular domains of GPVI or EMMPRIN so as to form a soluble receptor that is capable to inhibits the interaction between GPVI and EMMPRIN. Thus the functional equivalents include soluble forms of GPVI or EMMPRIN. A suitable soluble form of these proteins, or functional equivalents thereof, might comprise, for example, a truncated form of the protein from which the transmembrane domain has been removed by chemical, proteolytic or recombinant methods. In some embodiments, the polypeptide comprises consecutive amino acids having a sequence which corresponds to the sequence of at least a portion of an extracellular domain of GPVI, which portion binds to EMMPRIN. In some embodiments, the polypeptide comprises consecutive amino acids having a sequence which corresponds to the sequence of at least a portion of an extracellular domain of EMMPRIN, which portion binds to GPV1. In some embodiments, the polypeptide corresponds to an extracellular domain of GPVI or EMMPRIN.

In some embodiments, the functional equivalent is fused to a heterologous polypeptide to form a fusion protein. As used herein, a "fusion protein" comprises all or part (typically biologically active) of a functional equivalent of the present invention operably linked to a heterologous polypeptide (i.e., a polypeptide other than the same polypeptide). Within the fusion protein, the term "operably linked" is intended to indicate that the functional equivalent of the present invention and the heterologous polypeptide are fused in-frame to each other. The heterologous polypeptide can be fused to the N-terminus or C-terminus of the functional equivalent of the present invention. In some embodiments, the functional equivalent is fused to an immunoglobulin constant domain (Fc region) to form an immunoadhesin. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. In some embodiments, the Fc region is a native sequence Fc region. In some embodiments, the Fc region is a variant Fc region. In still another embodiment, the Fc region is a functional Fc region. As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The adhesion portion and the immunoglobulin sequence portion of the immunoadhesin may be linked by a minimal linker. The immunoglobulin sequence typically, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but typically IgG1 or IgG4. In some embodiments, the functional equivalent of GPVI and the immunoglobulin sequence portion of the immunoadhesin are linked by a minimal linker. As used herein, the term "linker" refers to a sequence of at least one amino acid that links the polypeptide of the invention and the immunoglobulin sequence portion. Such a linker may be useful to prevent steric hindrances. In some embodiments, the linker has 4; 5; 6; 7; 8; 9; 10; 11; 12; 13; 14; 15; 16; 17; 18; 19; 20; 21; 22; 23; 24; 25; 26; 27; 28; 29; 30 amino acid residues. However, the upper limit is not critical but is chosen for reasons of convenience regarding e.g. biopharmaceutical production of such polypeptides. The linker sequence may be a naturally occurring sequence or a non-naturally occurring sequence. If used for therapeutical purposes, the linker is typically non-immunogenic in the subject to which the immunoadhesin is administered. One useful group of linker sequences are linkers derived from the hinge region of heavy chain antibodies as described in WO 96/34103 and WO 94/04678. Other examples are poly-alanine linker sequences.

By a "therapeutically effective amount" is meant a sufficient amount of the agent for use in a method for the treatment of metastasis at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the severity of the cancer, the age, body weight, general health, sex and diet of the subject; the time of administration, route of administration, and rate of excretion of the specific compound employed; the duration of the treatment; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the agent of the present invention is administered to the subject in the form of a pharmaceutical composition. Typically, the agent of the present invention may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semisolid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The antibody of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1. Lack of GPVI inhibits tumor metastasis. (A) Schematic of an experimental metastasis model consisting of i.v. injection of AT-3 (B, C) or B16F10 (D) tumor cells in wildtype or $GPVI^{-/-}$ mice. (B) Representative hematoxylin-eosin stained sections obtained from lungs of B16F10-injected wildtype (WT) and GPVI-deficient mice ($GPVI^{-/-}$). Scale bar: 20 µm. (C, D) The bar graphs represent the quantification of the number of metastasis in lung tissue of mice injected with AT-3 (C) or with B16F10 (D) tumor cells. Mean±SEM, * p<0.05. (E) Schematic of a mouse orthotopic metastasis assay. AT-3 tumor cells were injected into the forth mammary fat pad of wildtype and GPVI-deficient mice, and the volume of primary tumor in the mammary fat pad, and the number of lung metastasis were determined. (F) The bar graph represents the primary tumor volume 30 days post-injection. (G) The bar graphs represent the quantification of the number of metastasis in lung tissue of WT and $GPVI^{-/-}$ mice 30 days post-injection of AT-3 cells. Mean±SEM, * p<0.05.

FIG. 2. GPVI is involved in platelet interaction with tumor cells. Platelet adhesion to tumor cells was quantified based on the fluorescence detection of RAM.1-labelled platelets (red). Representative epifluorescence microcopy images of RAM.1-Alexa-568 labelled mouse WT and $GPVI^{-/-}$ platelets (red) adhering to AT-3(A) or B16F10 (C) tumor cells. Scale Bar: 50 µm. The bar graphs represent the quantification of the fluorescent signal corresponding to the amount of platelets adhering AT-3(B) or B16F10 (D) tumor cells. Mean±SEM, *p<0.05. (E) Experimental design of the evaluation the role of GPVI in platelet/tumor cell interaction in vivo. $c-mpl^{-/-}$ mice were injected with RAM.1-cy3-labelled WT or $GPVI^{-/-}$ platelets (red) and CFSE-labelled AT-3 tumor cells (green). (F) 2 h post-injection, mice were euthanized, the lungs were collected and imaged to visualize the interaction of AT-3 tumor cells with platelets. Nuclei were stained with DAPI (blue). Scale Bar: 20 µm. (G) The bar graphs represent the number of tumor cells surrounded by platelets. Five mice per each group were used. Mean±SEM, *p<0.05, Mann-Whitney test. Mean±SEM, *p<0.05.

FIG. 3. EMMPRIN expressed on tumor cells supports GPVI-dependent platelet adhesion. Platelet adhesion to tumor cells was quantified based on the fluorescence detection of RAM.1-labelled platelets. (A) Representative epifluorescence microcopy images of RAM.1-Alexa-568 labelled mouse WT and $GPVI^{-/-}$ platelets (red) adhering to AT-3 tumor cells in the presence of a blocking anti-EMMPRIN or an isotype-matched control antibody. Scale Bar: 50 µm. (B) The bar graphs represent the quantification of the fluorescent signal corresponding to the amount of platelets adhering AT-3 tumor cells. Mean±SEM, *p<0.05. (C) Representative immunofluorescence images of WT and $GPVI^{-/-}$ mouse platelets adhering to recombinant soluble EMMPRIN under static conditions. Scale bar: 20 µm. (D) The bar graphs represent the quantification of WT and $GPVI^{-/-}$ mouse platelets adhered to immobilized soluble EMMPRIN. Mean±SEM, *** p<0.001, Mann-Whitney test.

EXAMPLE

Figure 1:
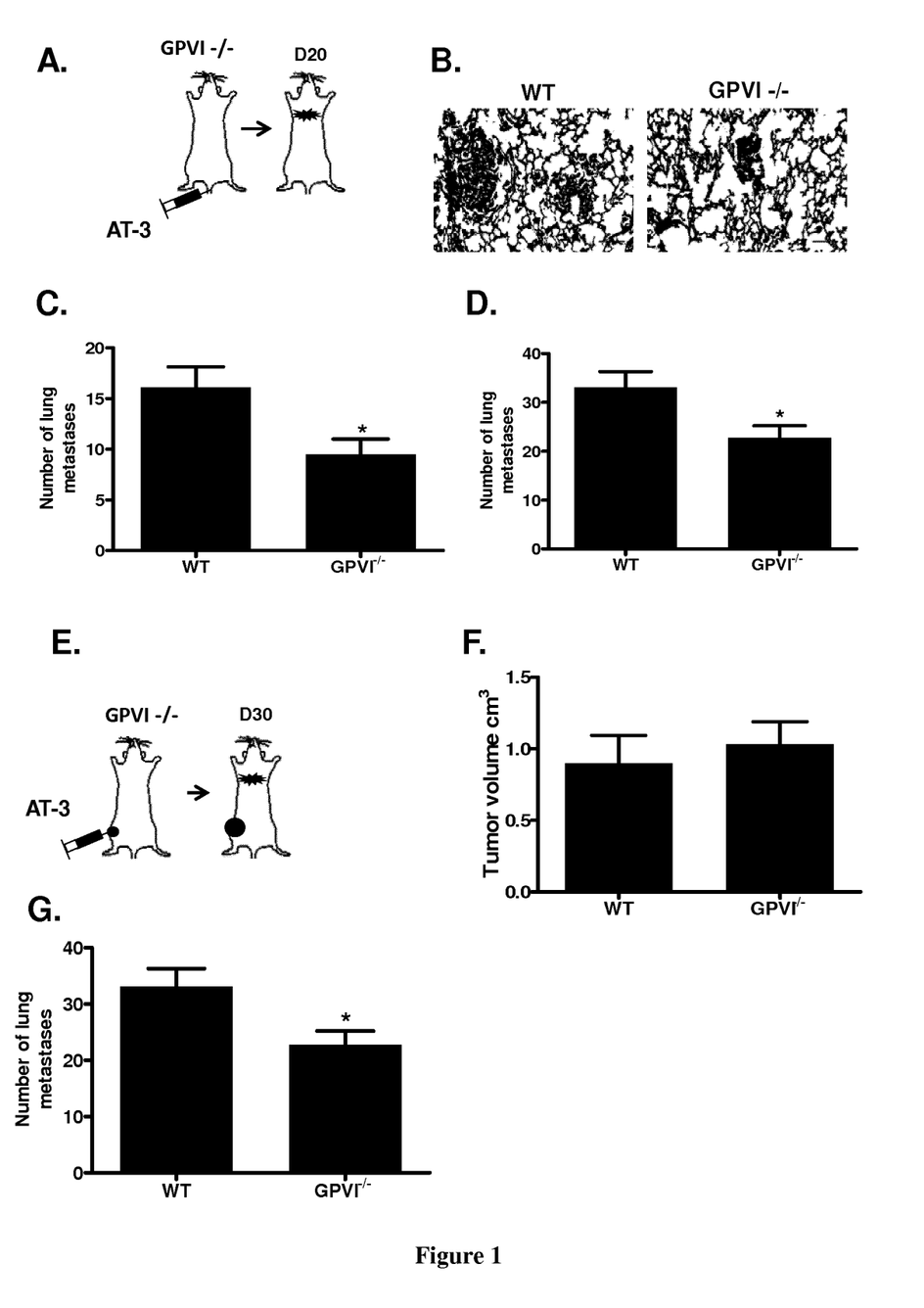
Figure 2:
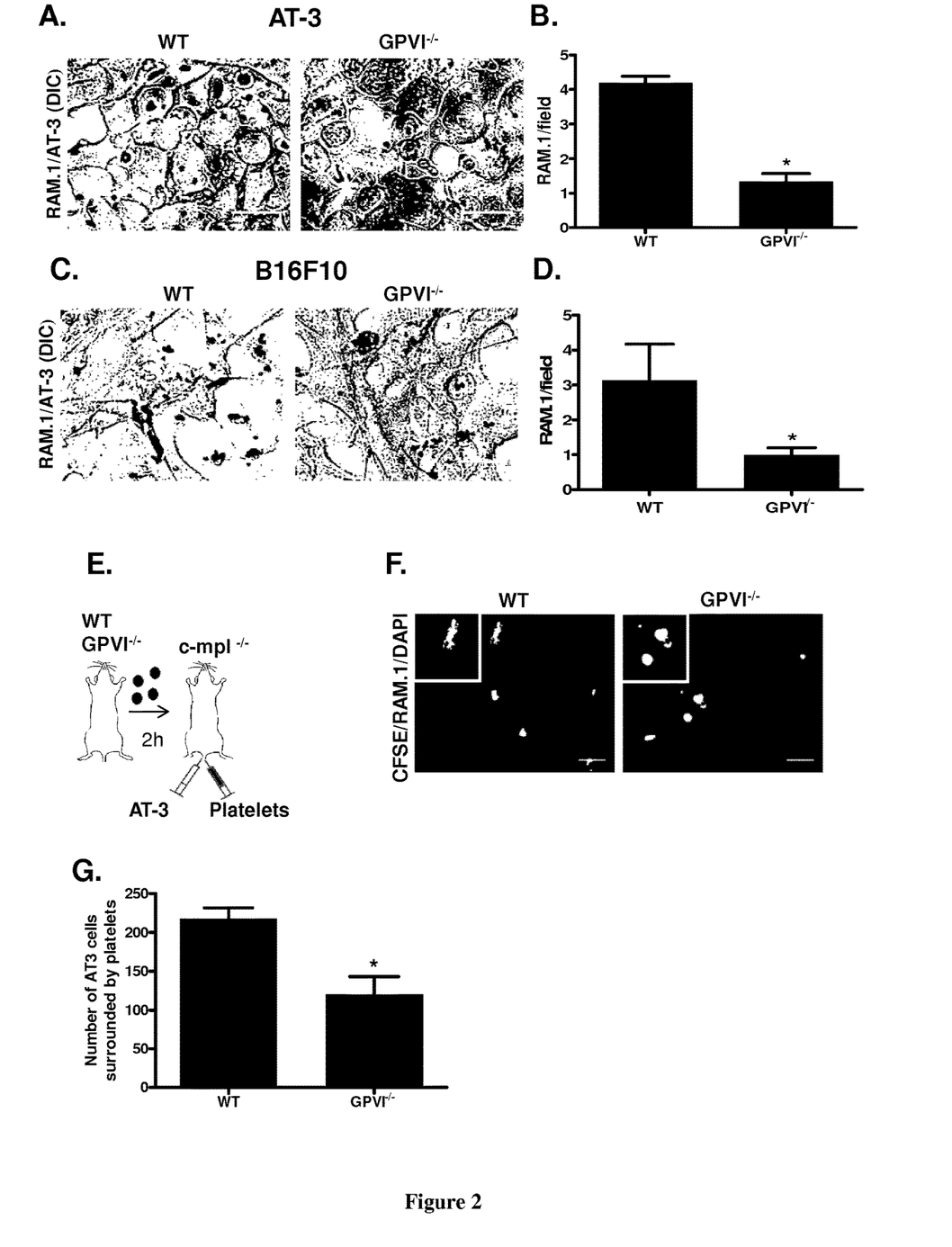
Figure 3:
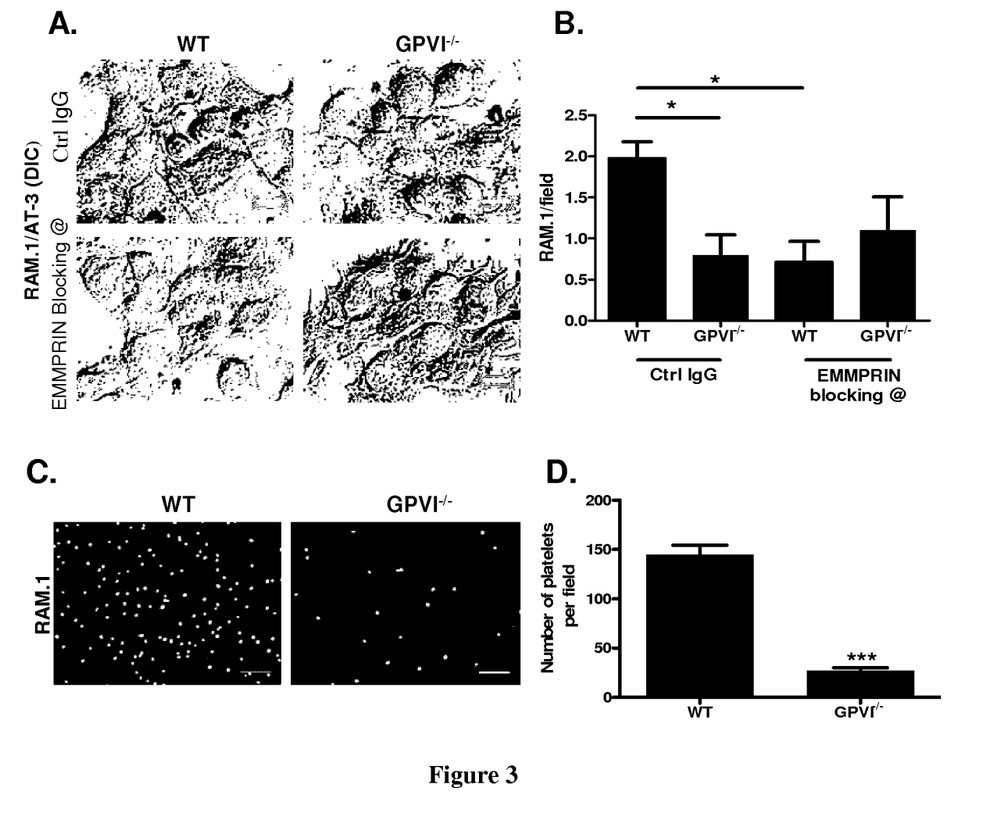
Figure 4:
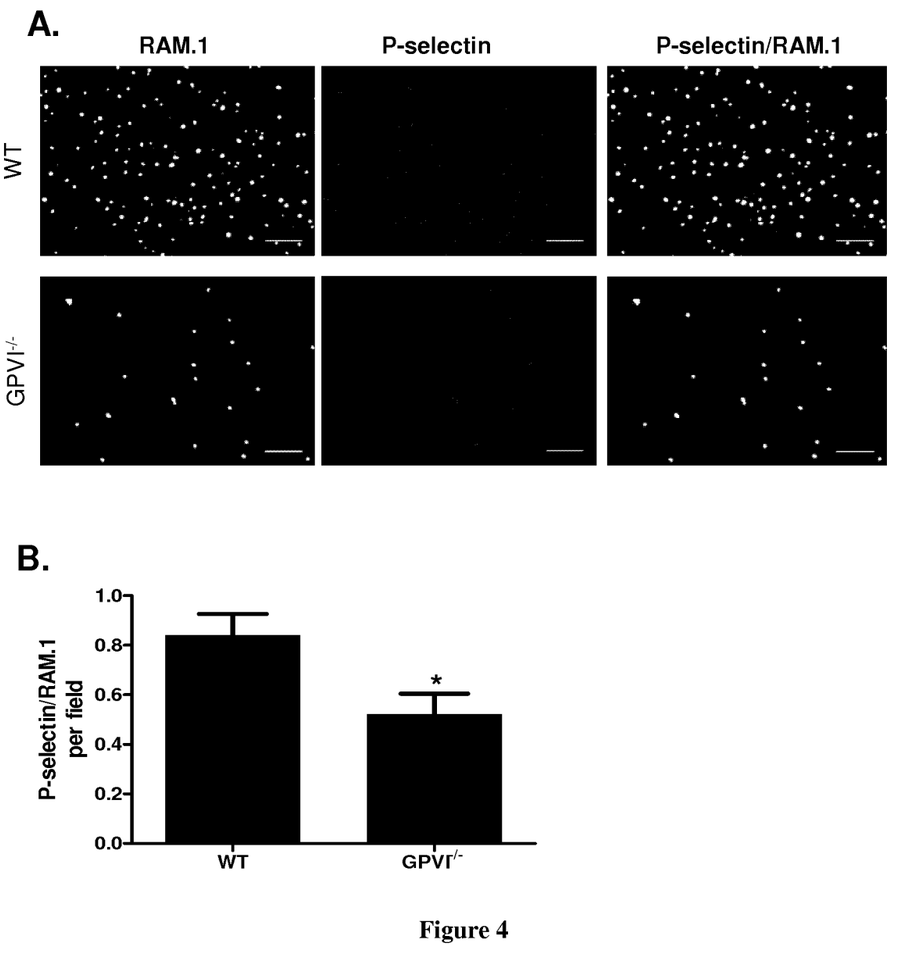
FIG. 4. EMMPRIN promoteds platelet granule release through GPVI. (A) Representative immunofluorescence microscopy images of WT and GPVI' mouse washed platelets adhering to recombinant EMMPRIN under static conditions. After 30 min, adherent platelets were stained with the anti-GPIbβ antibody, RAM.1 (green), and for P-selectin exposure (red). (B) The bar graphs represent quantification of the ratio between P-selectin and RAM.1 signals of adherent platelets. Mean±SEM, * p<0.05, Mann-Whitney test.
Figure 5:
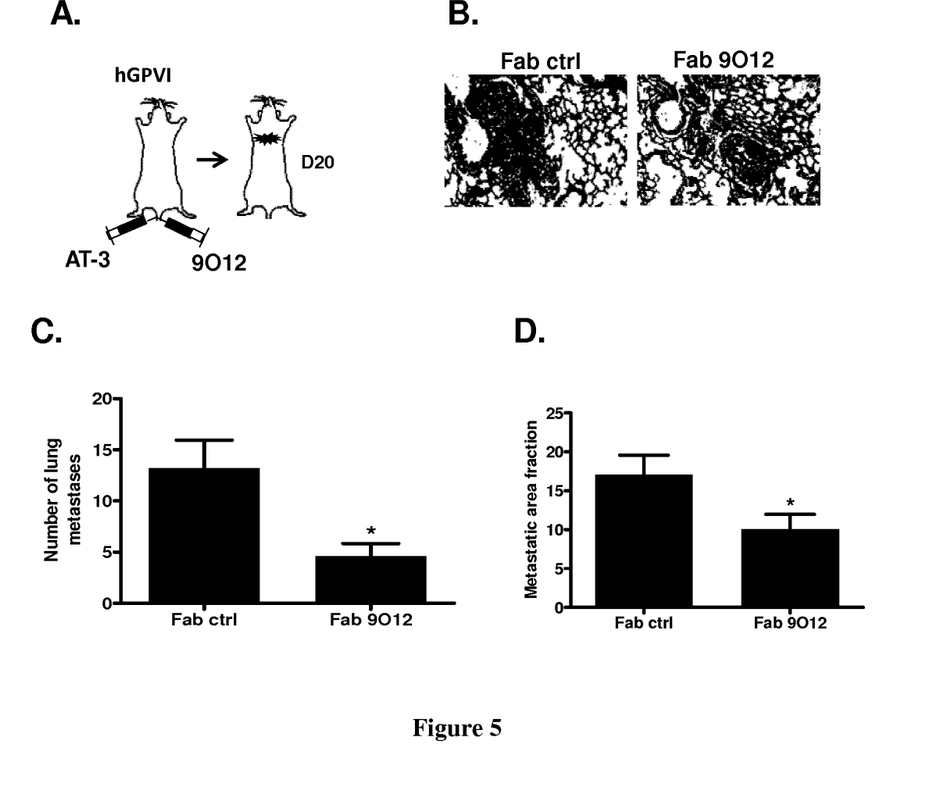
FIG. 5. Antibody-mediated blockade of GPVI inhibits tumor metastasis in a mouse model humanized for GPVI. (A) Schematic of an experimental metastasis model consisting of i.v. injection of AT-3 tumor cells in mice expressing human GPVI (hGPVI) together with the Fab fragment of the anti-GPVI blocking antibody, 9O12. (B) Representative hematoxylin-eosin stained sections obtained from lungs of hGPVI mice. Scale bar: 20 µm. (C) The bar graphs represent the quantification of the number of metastatic foci in lung tissue of mice injected with AT-3 tumor cells. Mean±SEM, * p<0.05. (D) The bar graphs represent the metastatic area fraction in lung tissue of mice injected with AT-3 tumor cells. Mean±SEM, * p<0.05.

We show that i.v. injection of metastatic cell lines into the tail vein of adult mice resulted in a marked decrease in lung metastasis in GPVI deficient mice as compared to controls (FIG. 1). Similar results were obtained in a spontaneous model in which tumor cells were injected in the mammary fat pad of adult female mice, forming primary tumors that subsequently metastasize to the lungs. We show that GPVI is involved in platetet interaction with tumor cells (FIG. 2) and this interaction is mediated by EMMPRIN (FIGS. 3 and 4). In particular an anti-EMMPRIN antibody decreases the adhesion of platelets to tumors cells (FIG. 3A). Finally we show that the Fab fragment of 9O12 prevents experimental metastases (FIG. 5).

REFERENCES

Throughout this application, various references describe the state of the art to which this invention pertains. The disclosures of these references are hereby incorporated by reference into the present disclosure.

The invention claimed is:

1. A method for inhibiting the development of metastases in a patient suffering from cancer, wherein the cancer is selected from the group consisting of bile duct cancer, bladder cancer, bone cancer, brain and central nervous system cancer, breast cancer, Castleman disease, cervical cancer, colorectal cancer, endometrial cancer, esophagus cancer, gallbladder cancer, gastrointestinal carcinoid tumors, Hodgkin's disease, non-Hodgkin's lymphoma, Kaposi's sarcoma, kidney cancer, laryngeal and hypopharyngeal cancer, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, stomach cancer, testicular cancer, thymus cancer, thyroid cancer, vaginal cancer, vulvar cancer, and uterine cancer, comprising administering to the subject a therapeutically effective amount of an anti-GPVI antibody, wherein said anti-GPVI antibody does not induce depletion of platelets, and wherein the anti-GPVI antibody comprises a heavy chain variable region comprising CDR1, CDR2 and CDR3 regions constituted of SEQ ID NO: 1, SEQ ID NO: 2, and SEQ ID NO: 3 and a light chain variable region comprising CDR1, CDR2 and CDR3 regions constituted of SEQ ID NO: 4, SEQ ID NO: 5, and SEQ ID NO: 6.

2. The method of claim 1 for inhibiting the development of lung metastases.

3. The method of claim 1 wherein the patient suffers from a breast cancer.

4. The method of claim 1 wherein the anti-GPVI antibody is a Fab fragment.

* * * * *